US011350968B2

United States Patent
Samuel et al.

(12) United States Patent
(10) Patent No.: US 11,350,968 B2
(45) Date of Patent: Jun. 7, 2022

(54) MODULAR BONE SCREW

(71) Applicant: LIFE SPINE, INC., Huntley, IL (US)

(72) Inventors: Forrest Samuel, Carlsbad, CA (US); Gregory Palagi, Geneva, IL (US)

(73) Assignee: LIFE SPINE, INC., Huntley, IL (US)

( * ) Notice: Subject to any disclaimer, the term of this patent is extended or adjusted under 35 U.S.C. 154(b) by 164 days.

(21) Appl. No.: 16/790,098

(22) Filed: Feb. 13, 2020

(65) Prior Publication Data

US 2020/0179015 A1 Jun. 11, 2020

Related U.S. Application Data

(63) Continuation of application No. 15/947,848, filed on Apr. 8, 2018, now Pat. No. 10,588,666.

(60) Provisional application No. 62/483,590, filed on Apr. 10, 2017.

(51) Int. Cl.
*A61B 17/70* (2006.01)
*A61B 17/86* (2006.01)
*A61B 90/00* (2016.01)

(52) U.S. Cl.
CPC ...... *A61B 17/7032* (2013.01); *A61B 17/7037* (2013.01); *A61B 17/863* (2013.01); *A61B 17/8605* (2013.01); *A61B 2090/037* (2016.02)

(58) Field of Classification Search
CPC ............ A61B 17/7032; A61B 17/7034; A61B 17/7035; A61B 17/7037; A61B 17/7038; A61B 17/704
USPC .................................................. 606/264–273
See application file for complete search history.

(56) References Cited

U.S. PATENT DOCUMENTS

| | | | |
|---|---|---|---|
| 8,628,558 B2 | 1/2014 | Harvey et al. | |
| 10,588,666 B2 * | 3/2020 | Samuel | A61B 17/8605 |
| 2012/0143266 A1 | 6/2012 | Jackson et al. | |
| 2014/0121703 A1 | 5/2014 | Jackson et al. | |
| 2016/0331412 A1 | 11/2016 | Biedermann et al. | |

FOREIGN PATENT DOCUMENTS

EP 2 985 001 A1 2/2016

OTHER PUBLICATIONS

International Search Report for PCT PCT/US2018/026646, dated Oct. 24, 2019, 12 pages.

* cited by examiner

*Primary Examiner* — Eduardo C Robert
*Assistant Examiner* — Christina Negrellirodriguez
(74) *Attorney, Agent, or Firm* — Foley & Lardner LLP

(57) ABSTRACT

A modular polyaxial bone screw includes a poly-axial bone screw, a polyaxial tulip head, and a collet disposed within the tulip head, the collet interacting with the bone screw and tulip head providing an interference fit with the bone screw head to lock orientation of the tulip head on and relative to the bone screw. Inner configurations of the tulip head interact with outer configurations of the collet to lock axial and/or rotational position of the collet within and relative to the tulip head, and thus about the bone screw head. The collet also has a resilient, tapered base with a plurality of slots in and about its end that allow the end to splay outwardly over and upon the head of the bone screw to create a snap or frictional interference fit between the splayed collet and the bone screw head when a spine rod is fixed in the tulip head.

10 Claims, 13 Drawing Sheets

MODULAR BONE SCREW

CROSS-REFERENCE TO RELATED APPLICATIONS

This application is a continuation of U.S. application Ser. No. 15/947,848, filed Apr. 8, 2018, which is hereby incorporated herein by reference in its entirety, and which claims the benefit of and/or priority under 35 U.S.C. § 119(e) to U.S. Application No. 62/483,590, filed Apr. 10, 2017, the entire contents of which is specifically incorporated herein by reference.

BACKGROUND

The present invention relates to spine screw assemblies for spine fixation and, more particularly, to modular bone screw assemblies for spinal rod applications.

Many people contend with orthopedic issues as a result of age, disease, and trauma, as well as congenital and acquired complications and conditions. While some of these issues can be alleviated without surgery, other issues respond better to surgery. In some cases, surgery may include the insertion of an orthopedic implant. Orthopedic spine assemblies and constructs such as spine plates, bone screw assemblies for spinal rods and other devices (spinal components) have made a profound contribution to the correction of spinal deformities, accidents and other problems in the cervical as well as thoracic, lumbar and sacral spine. These and other spinal devices are typically fixed to vertebrae using vertebral bone screws. Vertebral bone screws are specially designed and manufactured bone screws that are placed into the bone of a vertebra. Vertebral bone screws placed in the vertebra offer superior strength and pull-out resistance as compared to other forms of fixation in spine surgery. The ability to achieve vertebral fixation has allowed surgeons to obtain more secure fixation of the spinal components involved, which permits more powerful correction of spine problems and reported better clinical outcomes.

In addition to other uses, bone screws provide a solid foundation for the attachment of spinal rods. Spine rods are used for the fixation of a plurality of vertebrae for various situations. A spine rod is held relative to the vertebrae by a spine rod bone screw assembly. Various types of spine rod bone screw assemblies are known such as those that allow for inter-operative adjustments in the coronal, transverse and sagittal planes—generally known as poly-axial spine rod bone screw assemblies. Certain spine rod bone screw assemblies allow for various degrees of freedom of attachment of a spine rod thereto from any direction, angle, and height. In all cases, however, the spine rod bone screw assemblies hold a spine rod and are fixed to a vertebra. The poly-axial spine rod bone screw assembly thus permits spine rods to be rigidly locked into a variety of positions along with other types of implant components. This allows a surgeon to tailor-make each construct.

One type of poly-axial spine rod bone screw assembly is known as a poly-axial tulip head spine rod holder. The poly-axial tulip head spine rod holder consists of a poly-axial bone screw, a poly-axial head that is shaped like a tulip (poly-axial tulip head), and an insert within the poly-axial tulip head. The poly-axial tulip head is situated about the poly-axial bone screw head while the insert is situated within the poly-axial tulip head, the insert that interacts with the bone screw head and the tulip head. Downward pressure exerted against the insert during installation of a spine rod and set screw in the poly-axial tulip head causes the insert to bind against the poly-axial bone screw head and between the poly-axial tulip head such that the orientation of the tulip head is fixed relative to the bone screw. While current poly-axial tulip head spine rod holders are adequate, there is room for improvement.

Thus, there is a need for an improved poly-axial tulip head spine rod bone screw assembly.

SUMMARY

A modular poly-axial bone screw/screw assembly has three components, a poly-axial bone screw, a poly-axial tulip head, and an insert forming a collet disposed within the tulip head, the collet interacting with the tulip head to lock axial orientation of the collet within the tulip head and to provide a frictional interference fit with the bone screw head in order to lock orientation of the tulip head on and relative to the bone screw.

The tulip head has an inner configuration that interacts with the outer configuration of the collet to lock axial and/or rotational position of the collet within and relative to the tulip head, and thus about the bone screw head. The collet also has a resilient, tapered base with a plurality of slots in and about its end that allow the end to elastically splay outwardly over and upon the head of the bone screw to create a snap or frictional interference fit between the splayed collet and the bone screw head when a spine rod is fixed in the tulip head. An increase in spherical coverage created by the present configuration increases the amount of surface contact of the collet with the bone screw head. This allows for more controlled, uniform and secure orientation of the tulip head with respect to the bone screw.

In one form, the inner configuration of the tulip head comprises a plurality of projections protruding radially inwardly and spaced about the inner circumferential wall of the tulip head, while the outer configuration of the collet comprises a like plurality of depressions formed into its outer circumferential wall to receive the plurality of projections. Elastic deformation snap fits the collet within the tulip head. In another form, the plurality of projections are situated on the collet, and the plurality of depressions are situated in the inner circumferential wall of the tulip head, while the plurality of projections are situated on the outer conferential wall of the collet.

In another form, the inner configuration of the tulip head comprises a radially inwardly projecting lip extending about the inner circumferential wall of the tulip head creating an overhang and an undercut, while the outer configuration of the collet comprises a circumferential ledge. Other means may be used to lock the axial and/or rotational position of the collet in and to the tulip head.

The collet has an elastic/resilient base created at least in part by a plurality of cuts, slots, cutouts or the like that allows the poly-axial bone screw head to snap into the base of the collet thus causing a frictional interference fit. Particularly, the plurality of cuts in the base allows the elastic/resilient base of the collet to splay slightly during reception of the poly-axial bone screw head, then conform about the poly-axial bone screw head once pressure is applied by insertion of a spine rod and set screw into the tulip head, while the tapered end binds around, between and against the bone screw head and the inner wall of the tulip head.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The above mentioned and other features, advantages and objects of this invention, and the manner of attaining them, will become apparent and the invention itself will be better understood by reference to the following description of forms of the invention taken in conjunction with the accompanying drawings, wherein.

A description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Figure 10:
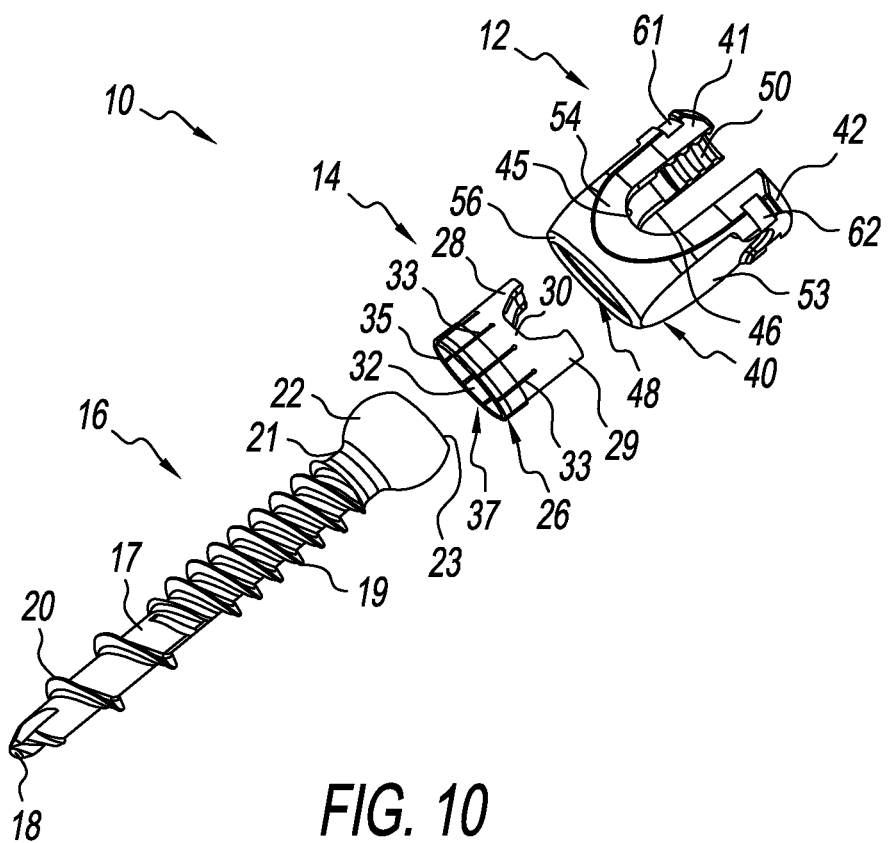
FIG. 10 is an exploded view of the modular poly-axial bone screw assembly of FIG. 1.
Figure 11:
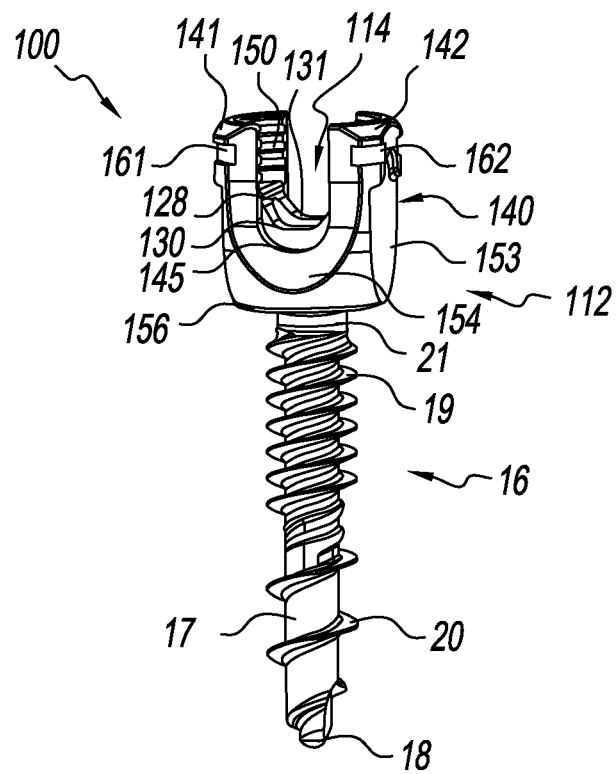
FIG. 11 is an isometric view of another form of a modular poly-axial bone screw assembly fashioned in accordance with the present principles.
Figure 12:
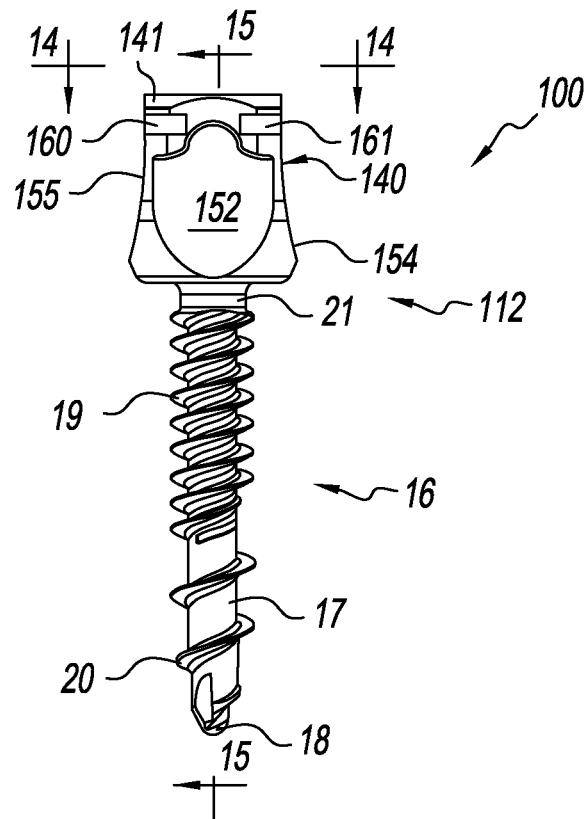
FIG. 12 is a side view of the modular poly-axial bone screw assembly of FIG. 11.
Figure 13:
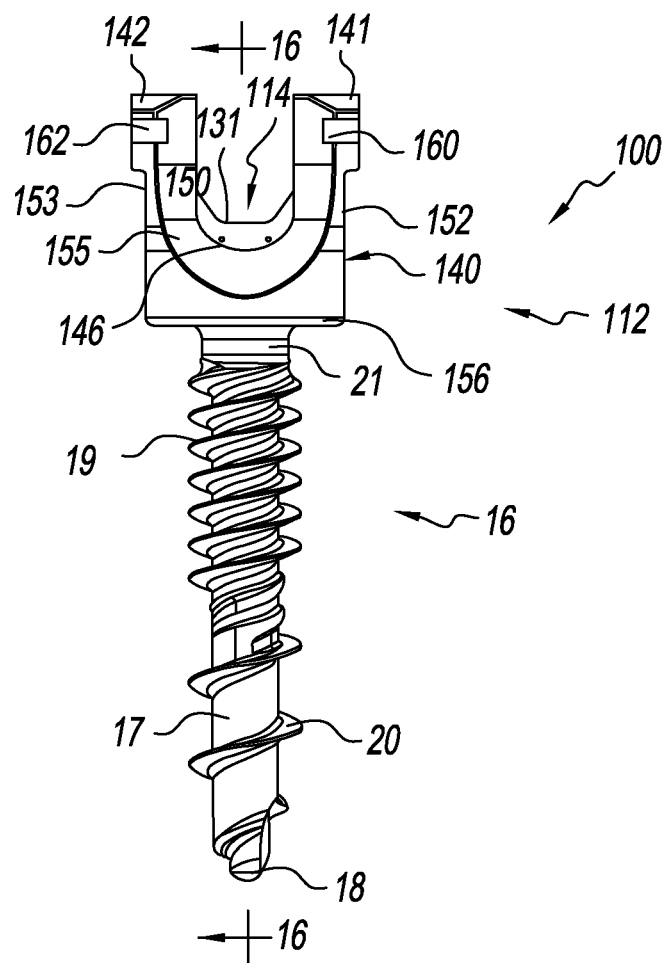
FIG. 13 is a another side view of the modular poly-axial bone screw assembly of FIG. 11, 90° to the side view of FIG. 11.
Figure 14:
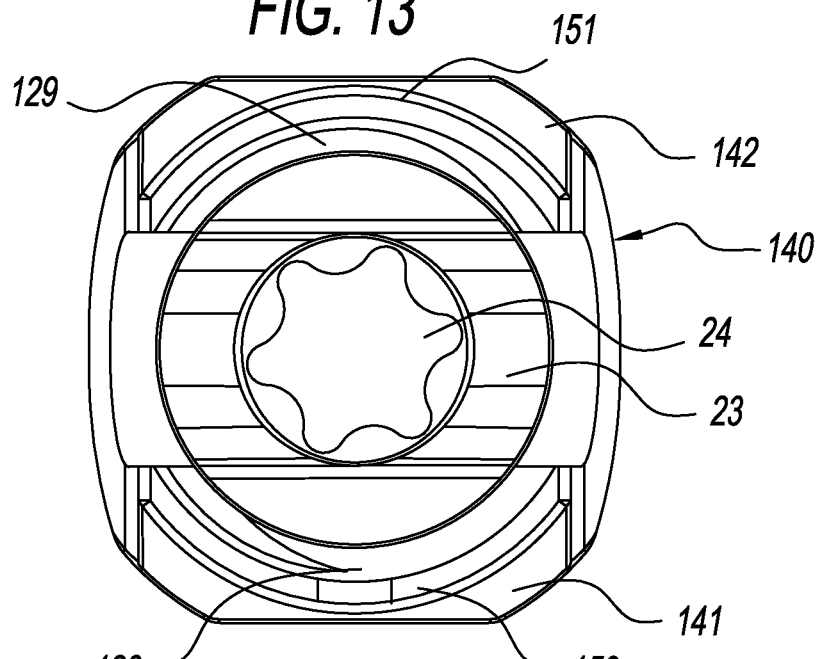
FIG. 14 is an enlarged top view of the modular poly-axial bone screw assembly of FIG. 11 taken along line 14-14 of FIG. 12.
Figure 15:
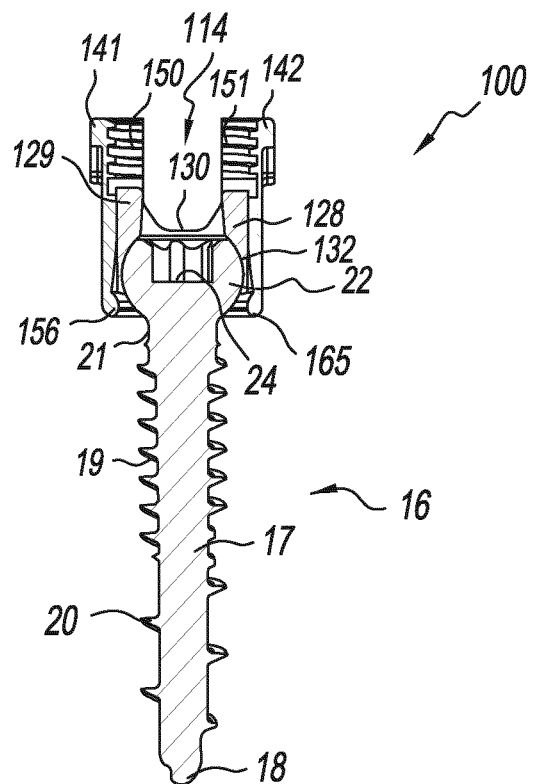
FIG. 15 is a sectional view of the modular poly-axial bone screw assembly of FIG. 11 taken along line 15-15 of FIG. 12.
Figure 16:
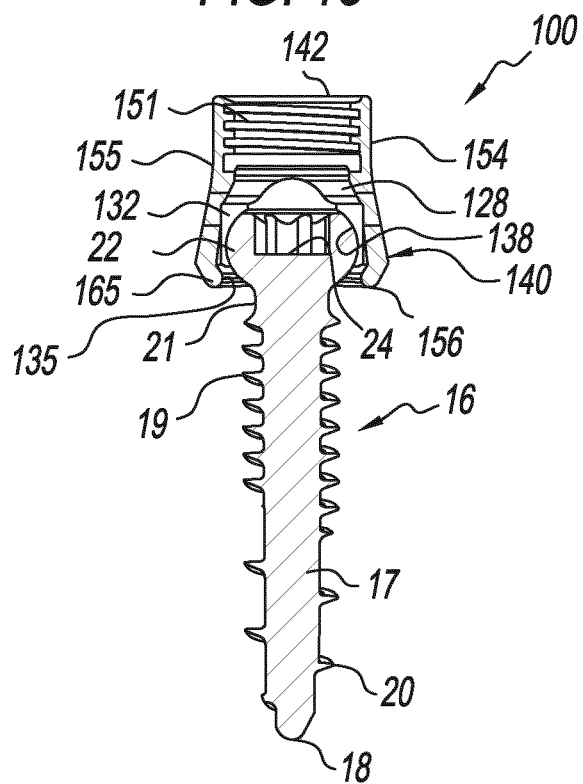
FIG. 16 is a sectional view of the modular poly-axial bone screw assembly of FIG. 11 taken along line 16-16 of FIG. 13.

Referring to FIGS. 1-10, there is depicted a form of modular poly-axial (polyaxial) bone screw/screw assembly ("modular poly-axial bone screw"), generally designated 10, for use in the spine and fashioned as described in the above Summary of the Invention, the modular poly-axial bone screw 10 for holding a spine rod (not shown) relative to the spine (not shown). FIG. 10 shows the three components of the poly-axial bone screw 10 in an exploded or pre-assembled view, the assemblage comprising a poly-axial bone screw ("bone screw") 16, a tulip head 12, and an insert/collet ("collet") 14.

The bone screw 16 has a generally globular (and therefore poly-axial) head 22 with a socket 24 in a top of the head 22 that is configured to receive a bone screw installation tool (not shown). In one form, the socket 24 is hexalobe-shaped and configured to receive a hexalobe bone screw installation tool. Other socket configurations may be used. A circumferential angle, slant, or taper 25 is preferably, but not necessarily, provided about the socket 24. A neck 21 projects from the head 22 opposite the socket 24. A shank 17 extends axially from the neck 21 and terminates in a tip 23. The shank 17 has first external threads/threading 20 along a lower portion of its axial length ("lower threading") proximate the tip 18, and second external threads/threading 19 along an upper portion of its axial length between the lower threading 20 and the neck 21. The shaft preferably, but not necessarily, increases in diameter from the tip 18 to the neck 21.

The tulip head 12 is defined by a generally tulip shaped body 40, having a bottom 56, a first side or sidewall 41 and a second side or sidewall 42, the second sidewall 42 opposite the first sidewall 41, the nomenclature first and second being arbitrary here and throughout unless otherwise indicated. The first sidewall 41 is generally arc-shaped and includes threads/threading 50 on its interior wall/surface. The second sidewall 42 is generally arc-shaped and includes threads/threading 51 on its interior wall/surface. The internal threading 50, 51 accepts a set screw (not shown) for fully seating the spine rod in the tulip head. The first sidewall 41 has an arcuate top 43 that is preferably, but not necessarily, sloped or slanted radially inwardly, and the second sidewall 41 likewise has an arcuate top 44 that is preferably, but not necessarily, sloped or slanted radially inwardly. The first sidewall 41 has a first flat 52 on its exterior surface extending generally from proximate the top 43 to the bottom 56. The first sidewall 41 further has a first notch 60 on one lateral side of the sidewall 41 proximate the top 43, and a second notch 61 on the other lateral side of the sidewall 41 proximate the top 43, the first and second notches permitting receipt of an installation tool (not seen) and otherwise. In like manner, the second sidewall 42 has a second flat 53 on its exterior surface extending generally from proximate the top 44 to the bottom 56. The second sidewall 42 further has a third notch 62 on one lateral side of the sidewall 42 proximate the top 44, and a fourth notch 63 on the other lateral side of the sidewall 42 proximate the top 44. The lower portion 64 of the body 40 is generally rounded.

The tulip head 12 has an interior bore 48 extending from a top to and through a bottom 56 of the body 20. The bore 48 receives the bone screw 16 and the collet 14. A spine rod reception area is defined in the body, formed as a first pocket, cutout or notch 45 between lateral sides of the first sidewall 41 and the second sidewall 42, and a second pocket, cutout or notch 46 between lateral sides of the first sidewall 41 and the second sidewall 42, the first and second pockets are opposite one another. The first and second notches 45, 46 are formed to receive a spine rod therein (not shown) and thus are generally arcuate or cup-shaped. The outside of the body 40 of the tulip head 12 surrounding the first notch 45 is a flat 54, while the outside of the body 40 of the second notch 46 is a flat 53. The internal threading 50, 51 of the first and second sidewalls 41, 42, provide for reception of a set screw or the like (not shown) that is used to "lock up" the tulip head 12 on and relative to the bone screw 16 via the collet 14.

Figure 1:
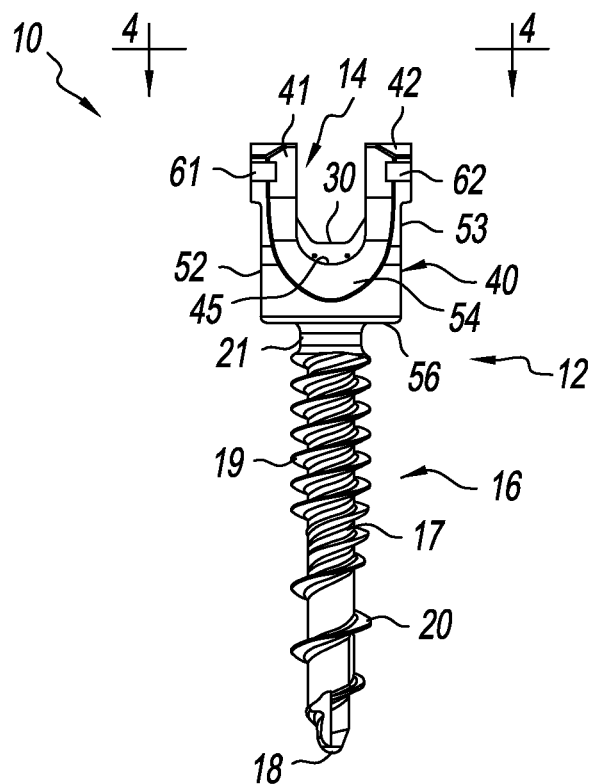
FIG. 1 is a side view of a form of a modular poly-axial bone screw assembly fashioned in accordance with the principles of the present invention.
Figure 2:
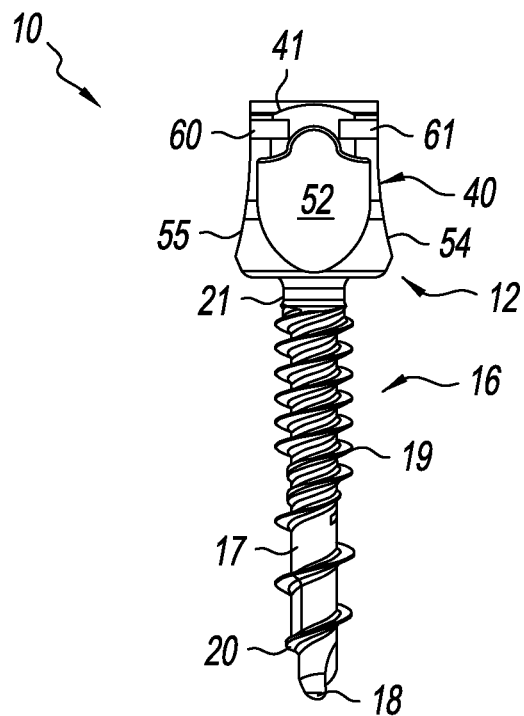
FIG. 2 is another side view of the modular poly-axial bone screw assembly of FIG. 1, 90° to the side view of FIG. 1.
Figure 3:
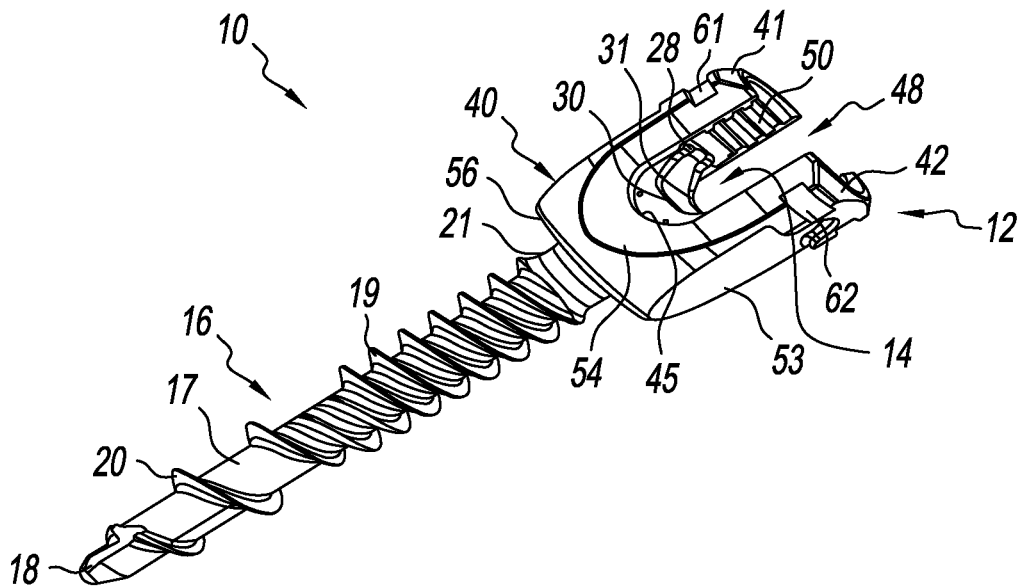
FIG. 3 is an isometric angled view of the modular poly-axial bone screw assembly of FIG. 1.
Figure 4:
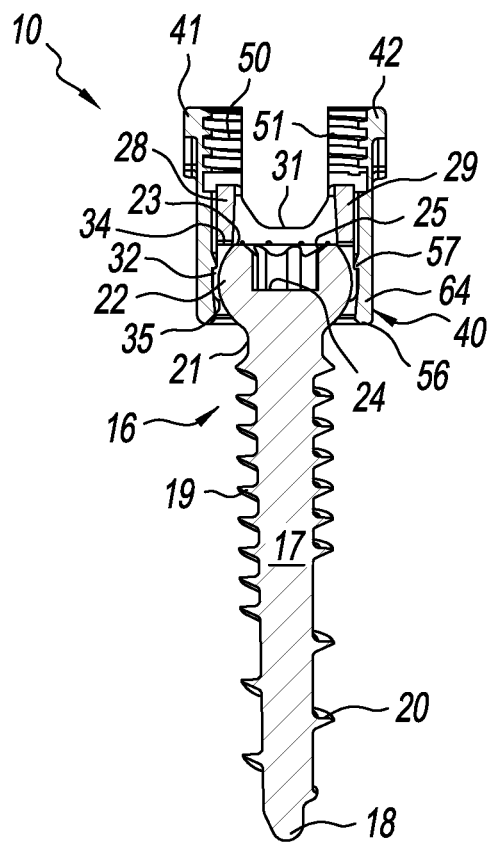
FIG. 4 is a sectional view of the modular poly-axial bone screw assembly of FIG. 1 taken along line 4-4 of FIG. 4.
Figure 5:
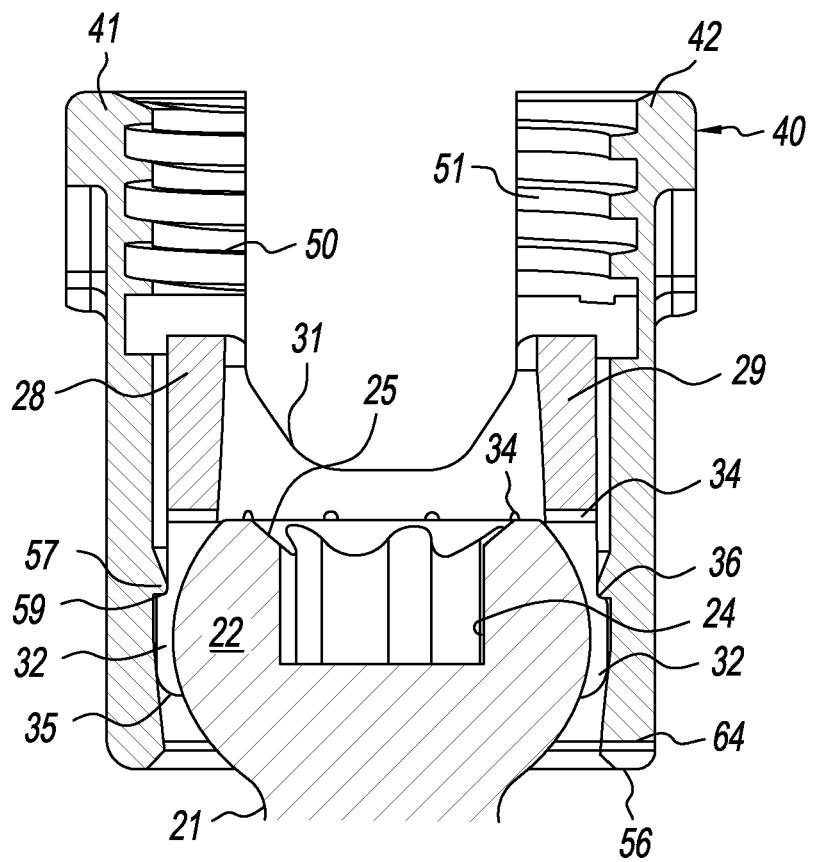
FIG. 5 is an enlarged sectional view of the tulip head and collet situated on the bone screw head of the modular poly-axial bone screw assembly of FIG. 1.
Figure 6:
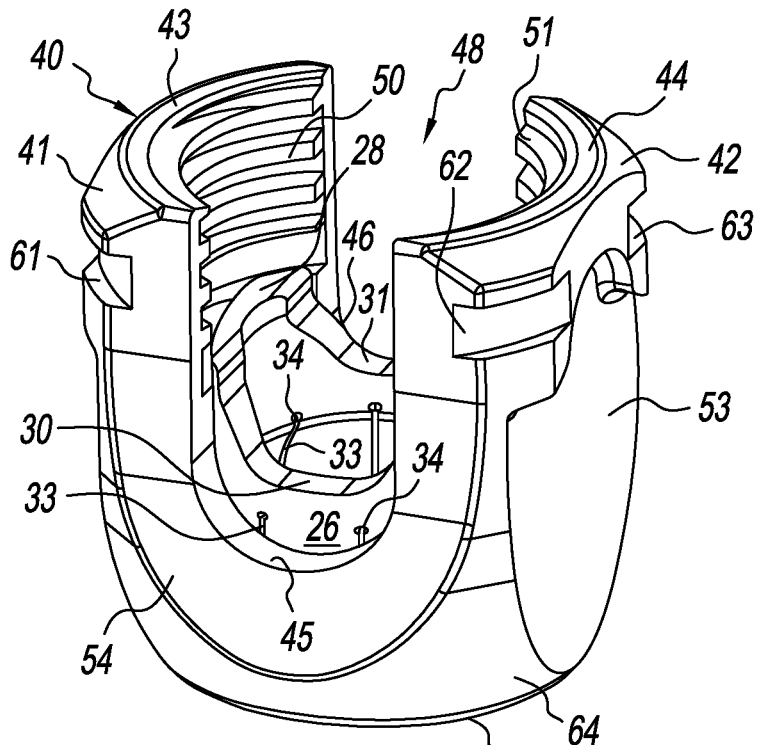
FIG. 6 is an enlarged isometric view of the collet assembled in the tulip head of the modular poly-axial bone screw assembly of FIG. 1.
Figure 7:
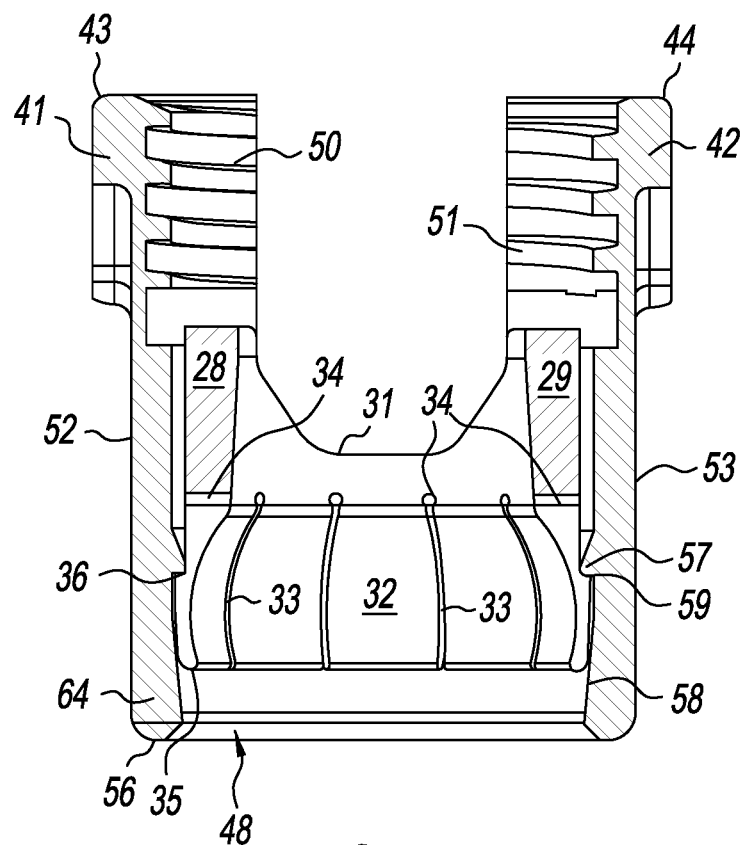
FIG. 7 is an enlarged sectional view of the assembled collet and tulip head of the modular poly-axial bone screw assembly of FIG. 1.
Figure 8:
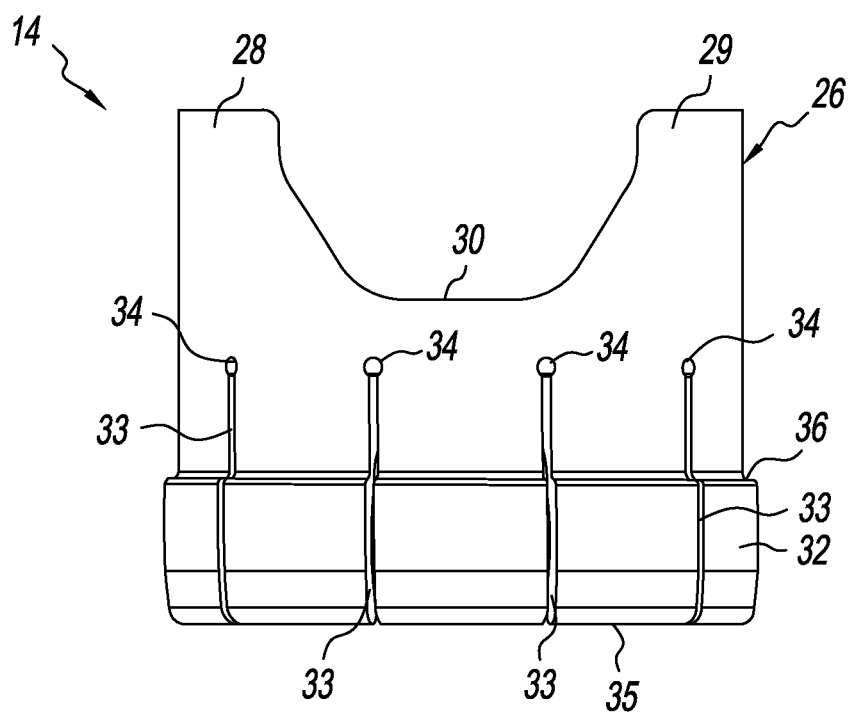
FIG. 8 is an enlarged side view of the collet of the modular poly-axial bone screw assembly of FIG. 1.
Figure 9:
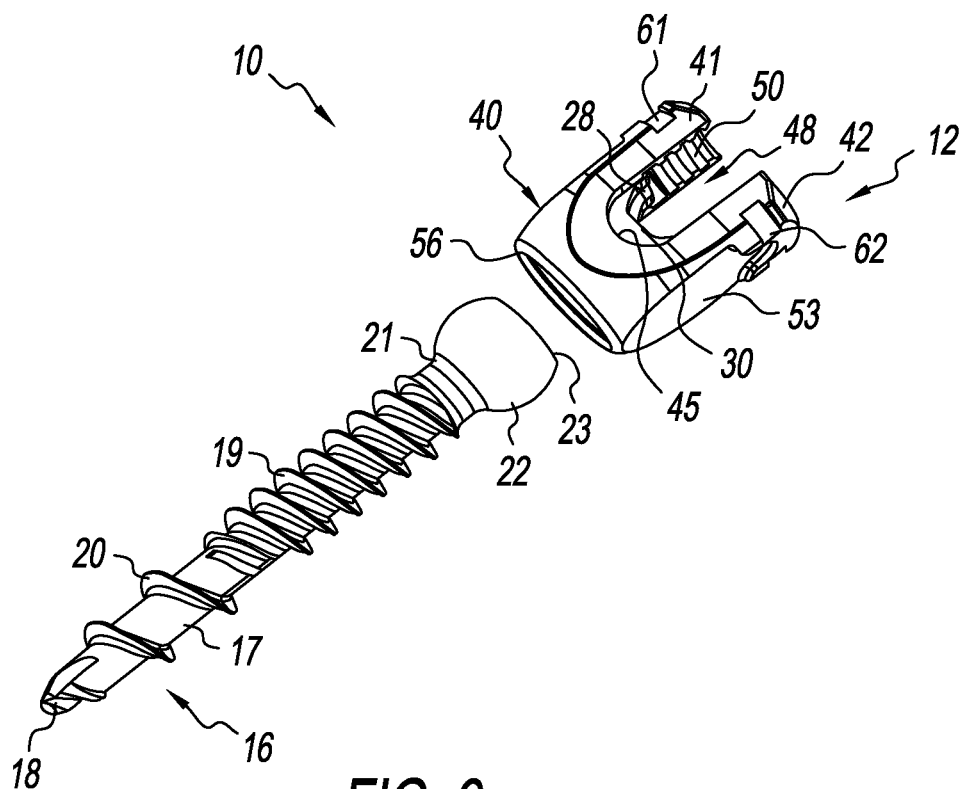
FIG. 9 is an exploded view of the assembled collect and tulip head relative to the bone screw of the modular poly-axial bone screw assembly of FIG. 1.

The inside of the tulip head 12 has an inner configuration best discerned in FIG. 5. Particularly, the inner configuration comprises a circumferential, radially inwardly projecting lip 57 extending about the lower inner circumferential wall of the tulip head, thereby creating an overhang and an undercut 59. Moreover, as discerned in the figure, the annular lower sidewall of the body 40 is preferably, but not necessarily, wider at the bottom 56.

The insert/collet 14 provides a taper lock and is defined by a generally cylindrical body 26 having a base or skirt 32 on a lower portion thereof, a first upstanding flange, side or sidewall 28, and a second upstanding flange, side or sidewall 29 that define a first pocket, cutout or notch 30 between lateral sides of the first and second upstanding flanges 28, 29, and a second pocket, cutout or notch 31 between opposite lateral sides of the first and second upstanding flanges 28, 29, the notches 30, 31 thus being oppositely disposed. The first and second notches 30, 31 are formed to receive a spine rod therein (not shown) and thus are generally arcuate or cup-shaped. An interior bore extends from a top of the body to a bottom 35 of the body. The bore allows access to the socket 24 of the bone screw head 22 of the poly-axial bone screw 16.

A bottom area 32 of the collet 14 includes a plurality of cuts, cutouts, notches or the like 33 that extend axially from the bottom 35 towards the upstanding flanges 28, 29. Each cut 33 is preferably, but not necessarily, equally circumferentially spaced about the bottom area 32 of the body 26 and terminates axially in a hole 34. The cuts 33 create a collet mechanism that allows the screw head 22 to snap into the bottom area 32 of the collet 14 thus creating a frictional interference fit. It should be appreciated that the number of cuts 33 may vary from two (2) to as many as desired. It is also preferable, but not necessary, that the cuts 33 are evenly spaced about the bottom area 32. The cuts 33 create a resilient or elastic interference or snap on fit with the polyaxial screw head 22 by allowing the bottom area 32 to splay slightly then from back around the screw head 22. The spherical coverage of the head 22 increases the amount of surface contact between the bottom area 32 of the collet 14 and the polyaxial screw head 22.

The outside of the collet 14 has an outer configuration best discerned in FIG. 5. Particularly, the outer configuration comprises a ledge 36 extending circumferentially about the body 26 proximate the bottom area 32. Because of the elastic nature of the collet 14, the projecting lip 57 of the tulip head 12 is captured by/on the ledge 36.

Referring to FIGS. 11-28, there is depicted another form of a modular poly-axial (polyaxial) bone screw/screw assembly ("modular poly-axial bone screw"), generally designated 100, for use in the spine and fashioned as described in the above Summary of the Invention, the modular poly-axial bone screw 100 for holding a spine rod (not shown) relative to the spine (not shown). In like form as the modular poly-axial bone screw 10 of FIGS. 1-10, the modular poly-axial bone screw 100 has three components, namely the poly-axial bone screw ("bone screw") 16 as described above, a tulip head 112, and an insert/collet ("collet") 114.

The tulip head 112 is defined by a generally tulip shaped body 140, having a bottom 156, a first side or sidewall 141 and a second side or sidewall 142, the second sidewall 142 opposite the first sidewall 141, the nomenclature first and second being arbitrary here and throughout unless otherwise indicated. The first sidewall 141 is generally arc-shaped and includes threads/threading 150 on its interior wall/surface. The second sidewall 142 is generally arc-shaped and includes threads/threading 151 on its interior wall/surface. The internal threading 150, 151 accepts a set screw (not shown) for fully seating the spine rod in the tulip head. The first sidewall 141 has an arcuate top 143 that is preferably, but not necessarily, sloped or slanted radially inwardly, and the second sidewall 141 likewise has an arcuate top 144 that is preferably, but not necessarily, sloped or slanted radially inwardly. The first sidewall 141 has a first flat 152 on its exterior surface extending generally from proximate the top 143 to the bottom 156. The first sidewall 141 further has a first notch 160 on one lateral side of the sidewall 141 proximate the top 143, and a second notch 161 on the other lateral side of the sidewall 141 proximate the top 143, the first and second notches permitting receipt of an installation tool (not seen) and otherwise. In like manner, the second sidewall 142 has a second flat 153 on its exterior surface extending generally from proximate the top 144 to the bottom 156. The second sidewall 142 further has a third notch 162 on one lateral side of the sidewall 142 proximate the top 144, and a fourth notch 163 on the other lateral side of the sidewall 142 proximate the top 144. The lower portion 164 of the body 140 is generally rounded.

The tulip head 112 has an interior bore 148 extending from a top to and through a bottom 156 of the body 120. The bore 148 receives the bone screw 116 and the collet 114. A spine rod reception area is defined in the body, formed as a first pocket, cutout or notch 145 between lateral sides of the first sidewall 141 and the second sidewall 142, and a second pocket, cutout or notch 146 between lateral sides of the first sidewall 141 and the second sidewall 142, the first and second pockets are opposite one another. The first and second notches 145, 146 are formed to receive a spine rod therein (not shown) and thus are generally arcuate or cup-shaped. The outside of the body 140 of the tulip head 112 surrounding the first notch 145 is a flat 154, while the outside of the body 140 of the second notch 146 is a flat 153. The internal threading 150, 151 of the first and second sidewalls 141, 142, provide for reception of a set screw or the like (not shown) that is used to "lock up" the tulip head 112 on and relative to the bone screw 116 via the collet 114.

Figure 17:
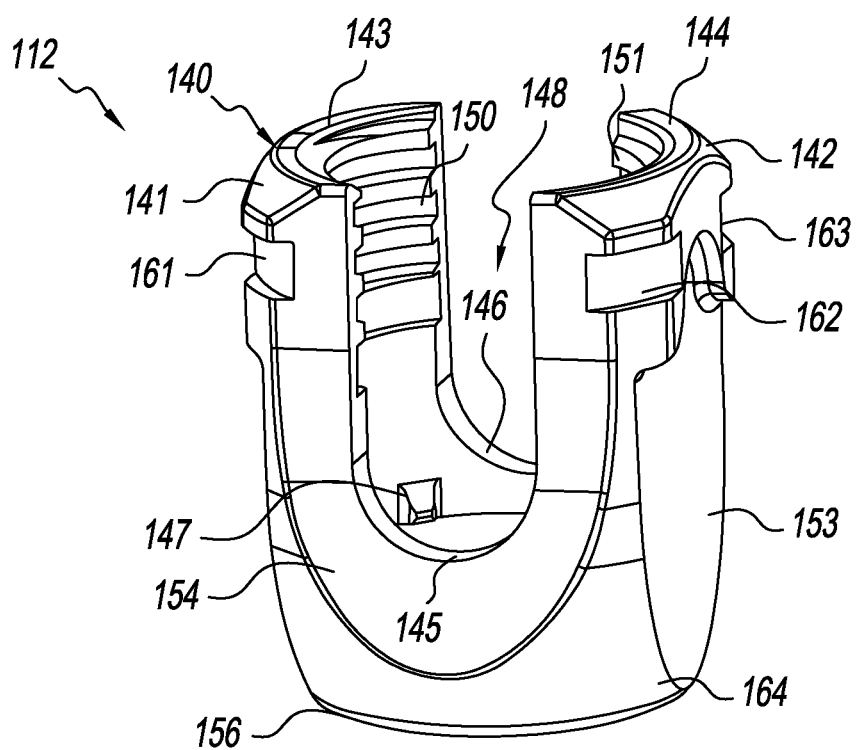
FIG. 17 is an enlarged isometric view of the tulip head of the modular poly-axial bone screw assembly of FIG. 11.
Figure 18:
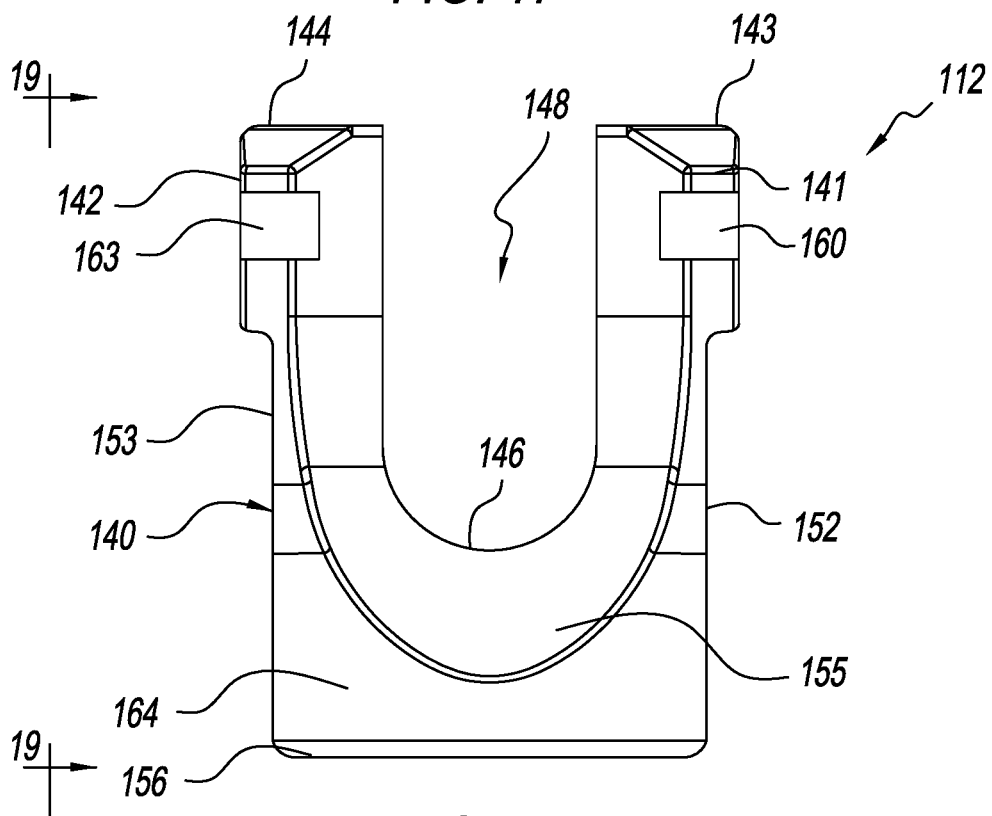
FIG. 18 is an enlarged side view of the tulip head of the modular poly-axial bone screw assembly of FIG. 11.
Figure 19:
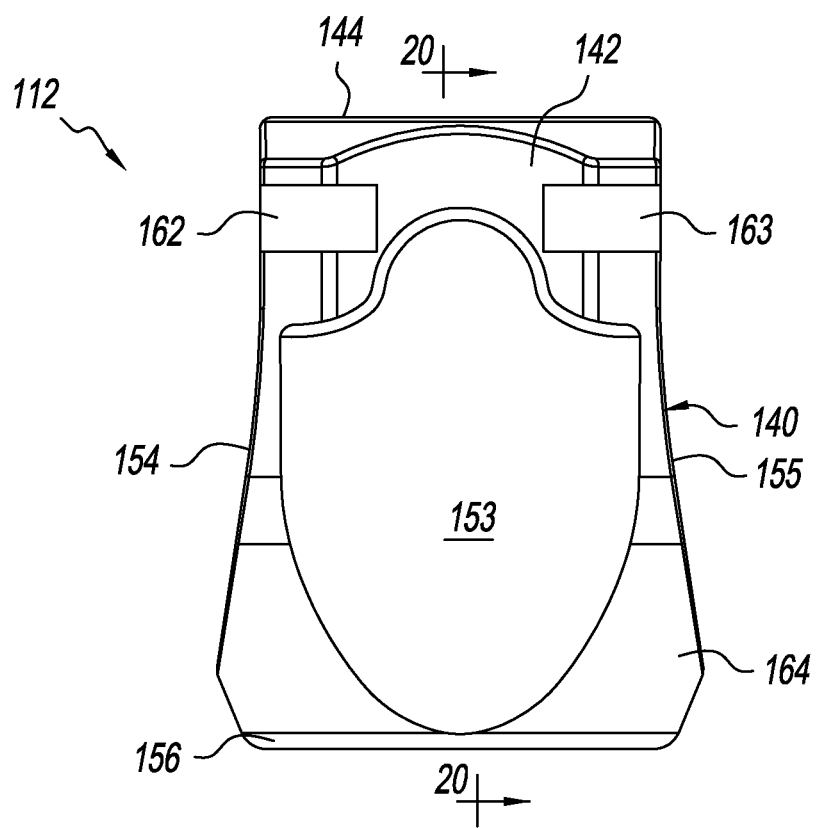
FIG. 19 is another side view of the tulip head of the modular poly-axial bone screw assembly of FIG. 11 taken along line 19-19 of FIG. 18.
Figure 20:
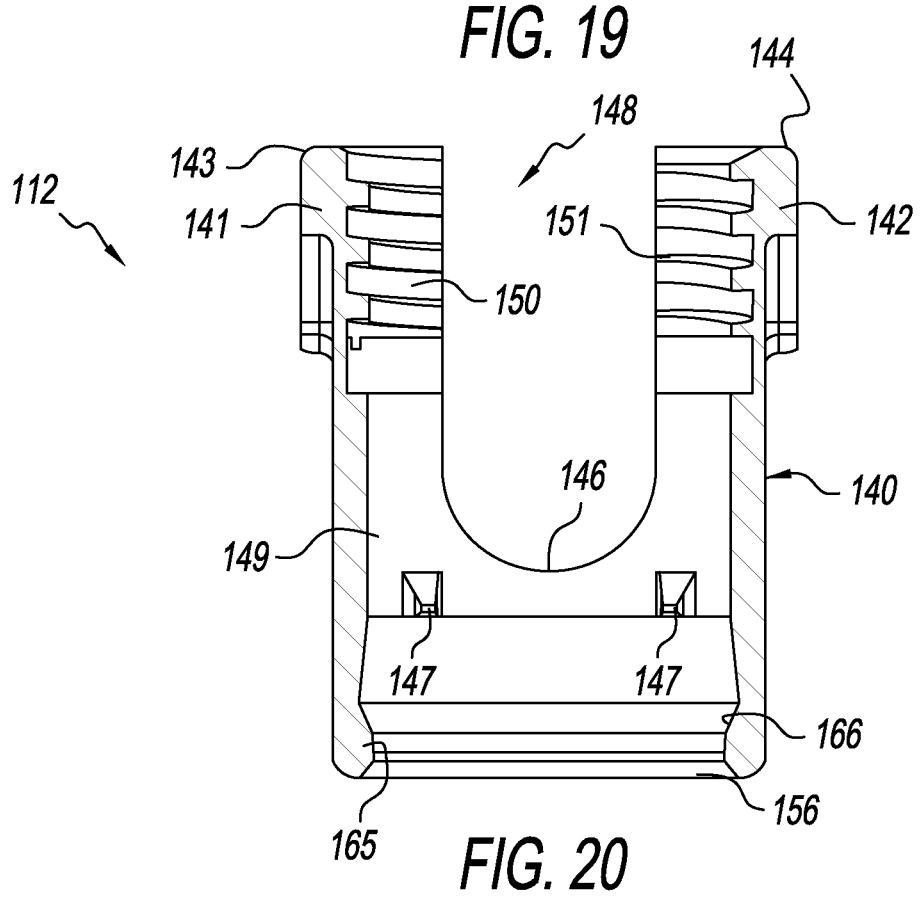
FIG. 20 is a sectional view of the tulip head of the modular poly-axial bone screw assembly of FIG. 11 taken long line 20-20 of FIG. 19.
Figure 21:
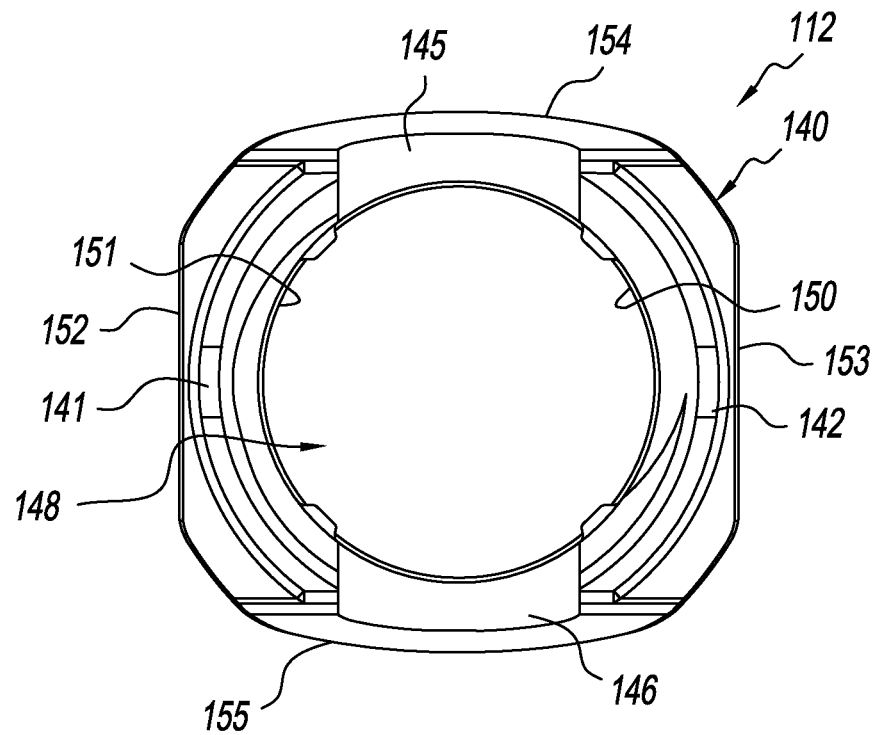
FIG. 21 is an enlarged top view of the tulip head of the modular poly-axial bone screw assembly of FIG. 11.

The inside of the tulip head 112 has an inner configuration best discerned in FIG. 17. Particularly, the inner configuration comprises a plurality of radially inwardly projecting protuberances 147 extending about the lower inner circumferential wall of the tulip head. While four (4) protuberances 147 are shown, any number may be used. Moreover, the configuration of the protuberances may be changed as necessary. The annular lower sidewall of the body 140 is preferably, but not necessarily, wider at the bottom 156.

The insert/collet 114 provides a taper lock and is defined by a generally cylindrical body 126 having a base or skirt 132 on a lower portion thereof, a first upstanding flange, side or sidewall 128, and a second upstanding flange, side or sidewall 129 that define a first pocket, cutout or notch 130 between lateral sides of the first and second upstanding flanges 128, 129, and a second pocket, cutout or notch 131 between opposite lateral sides of the first and second upstanding flanges 128, 129, the notches 130, 131 thus being oppositely disposed. The first and second notches 130, 131 are formed to receive a spine rod therein (not shown) and thus are generally arcuate or cup-shaped. An interior bore extends from a top of the body to a bottom 135 of the body. The bore allows access to the socket 124 of the bone screw head 122 of the poly-axial bone screw 116.

A bottom area 132 of the collet 114 includes a plurality of cuts, cutouts, notches or the like 133 that extend axially from the bottom 135 towards the upstanding flanges 128, 129. Each cut 133 is preferably, but not necessarily, equally circumferentially spaced about the bottom area 132 of the body 126 and terminates axially in a hole 134. The cuts 133 create a collet mechanism that allows the screw head 122 to snap into the bottom area 132 of the collet 114 thus creating a frictional interference fit. It should be appreciated that the number of cuts 133 may vary from two (2) to as many as desired. It is also preferable, but not necessary, that the cuts 133 are evenly spaced about the bottom area 132. The cuts 133 create a resilient or elastic interference or snap on fit with the polyaxial screw head 122 by allowing the bottom area 132 to splay slightly then from back around the screw head 122. The spherical coverage of the head 122 increases the amount of surface contact between the bottom area 132 of the collet 114 and the polyaxial screw head 122.

Figure 22:
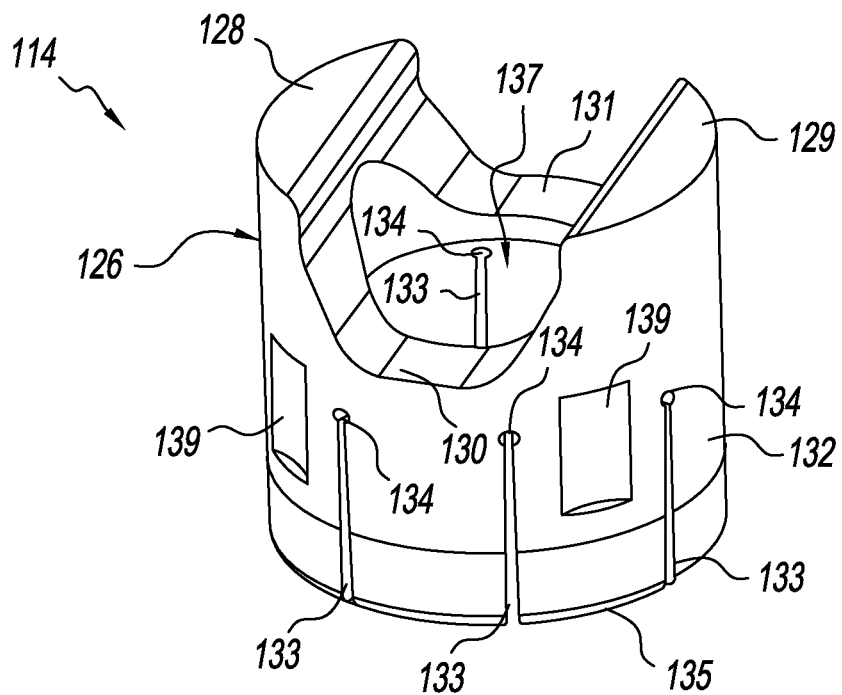
FIG. 22 is an isometric view of the collet of the modular poly-axial bone screw assembly of FIG. 11.
Figure 23:
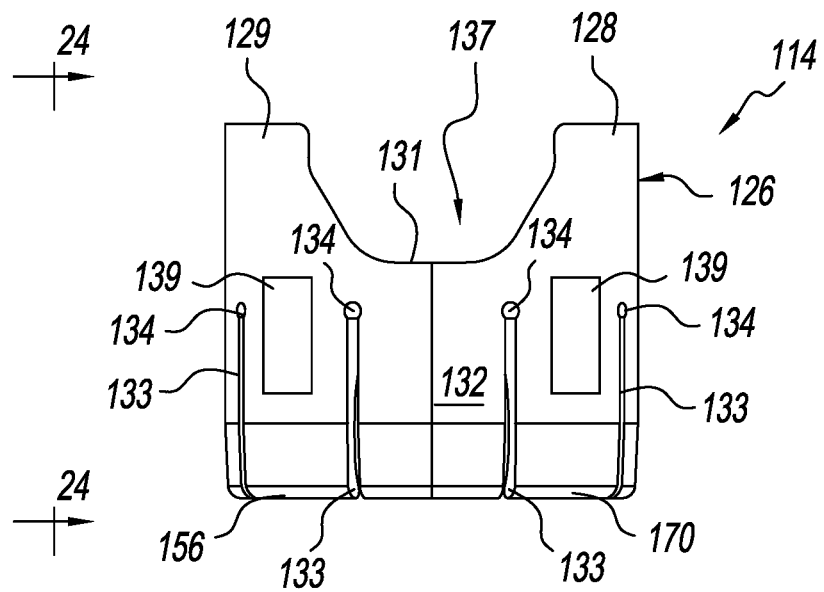
FIG. 23 is a side view of the collet of the modular poly-axial bone screw assembly of FIG. 11.
Figure 24:
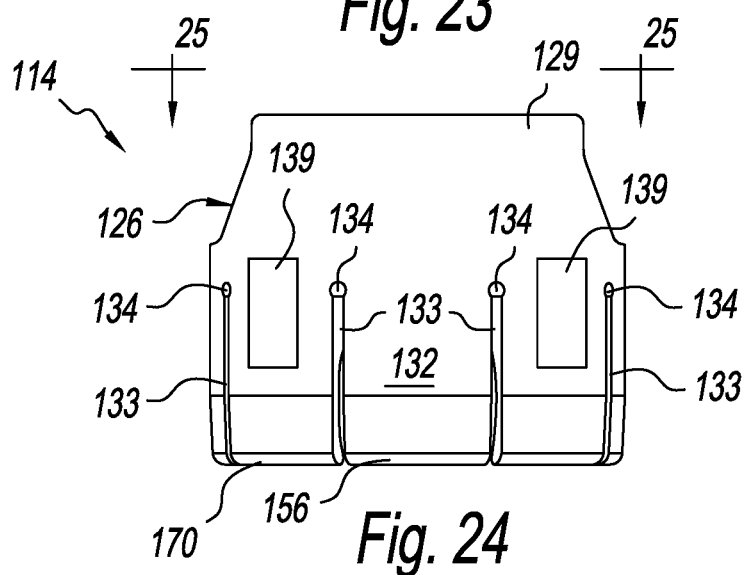
FIG. 24 is another side view of the collet of the modular poly-axial bone screw assembly of FIG. 11 taken along line 24-24 of FIG. 23.
Figure 25:
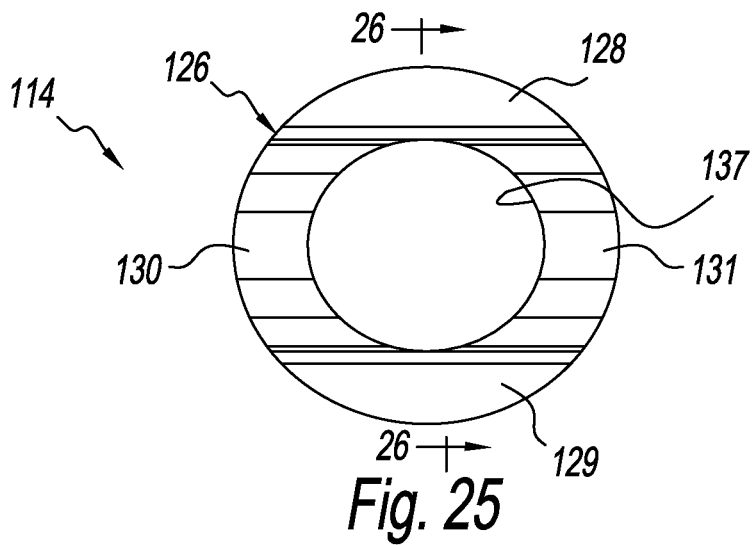
FIG. 25 is a top view of the collet of the modular poly-axial bone screw assembly of FIG. 11 taken along line 25-25 of FIG. 24.
Figure 26:
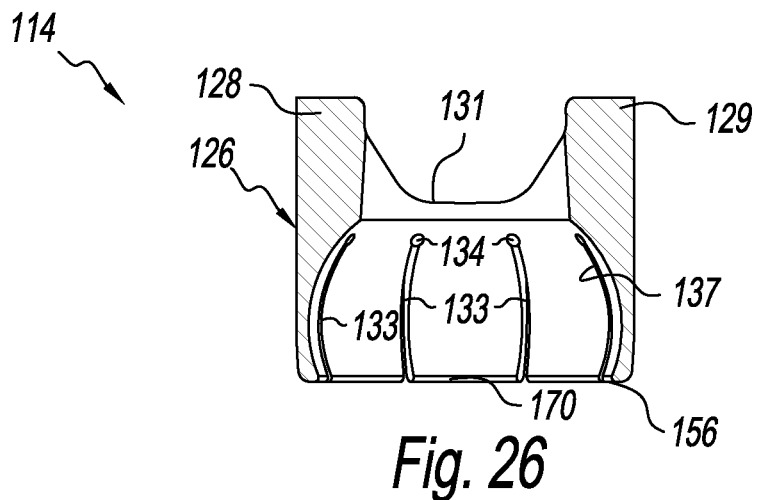
FIG. 26 is a sectional view of the collet of the modular poly-axial bone screw assembly of FIG. 11 taken along line 26-26 of FIG. 25.
Figure 27:
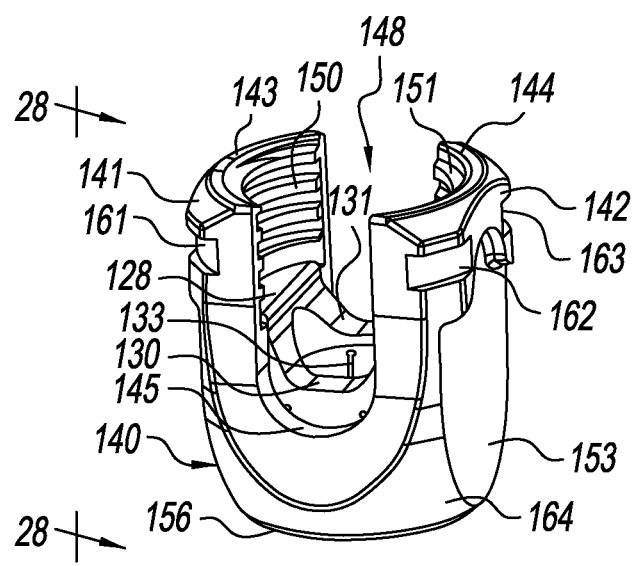
FIG. 27 is an isometric view of an assembly of the collet and tulip head of the modular poly-axial bone screw assembly of FIG. 11.
Figure 28:
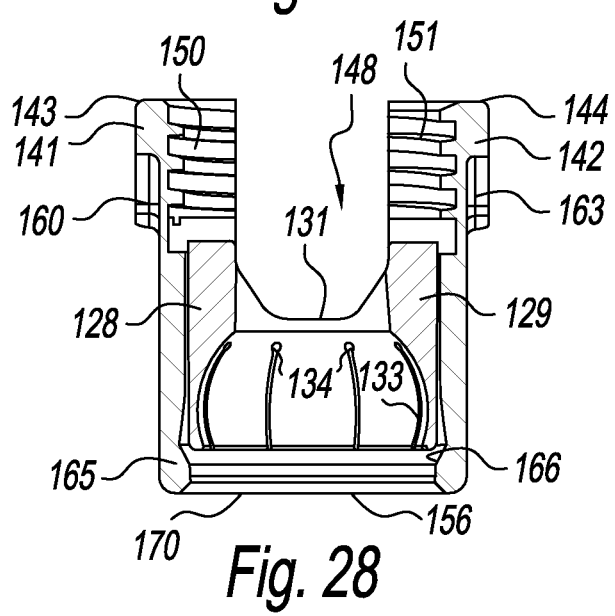
FIG. 28 is a section view of the collet and tulip head assembly of the modular poly-axial bone screw assembly of FIG. 11 taken along line 28-28 of FIG. 27.

The outside of the collet 114 has an outer configuration best discerned in FIG. 22. Particularly, the outer configuration comprises a plurality of depression, cutouts or the like 139 extending about the lower outer circumferential wall of the collet. The number of depressions 139 correspond in number to the plurality of protuberances 147 of the tulip head 112. While four (4) depressions 139 are shown, any number may be used. Moreover, the configuration of the depressions may be changed as necessary.

The various components of the modular poly-axial bone screws 10, 100 are made from a bio-compatible material such as, but not limited to, PEEK, other polymers/plastics, titanium, stainless steel, and alloys of same. Other bio-compatible materials, or course, may be used.

While the invention has been illustrated and described in detail in the drawings and foregoing description, the same is to be considered as illustrative and not restrictive in character, it being understood that only preferred forms have been shown and described and that all changes and modifications that come within the spirit of the invention are desired to be protected.

What is claimed is:

1. A modular bone screw assembly for holding a spine rod in a fixed spatial orientation relative to vertebral bone, the modular bone screw assembly comprising:
    a bone screw having a threaded shank and a screw head;
    a rod holder disposed on the screw head and configured to move relative to the screw head before the rod holder is fixed in spatial orientation relative to the bone screw, and configured to receive and hold a spine rod as the spatial orientation of the rod holder is fixed, the rod holder having a bore extending from a first end of the rod holder to a second end of the rod holder and having an upper portion, inner threading for threaded receipt of a set screw, and a lower portion sized to receive the head of the bone screw in its entirety; and
    a collet disposed in the interior of the rod holder, the collet having a lower section of a first diameter with a first end resting about the screw head and configured to splay on the screw head and fix a spatial orientation of the rod holder relative to the bone screw through interference between the first end, the screw head, and the rod holder when a spine rod is received in and affixed to the rod holder by the set screw, and an upper section of a second diameter that is smaller than the first diameter of the lower section;
    wherein one of the rod holder and the collet includes a lip extending therefrom, and the other of the rod holder and collet includes a ledge that captures the lip to retain the collet in its axial position.

2. The bone screw assembly of claim 1, wherein the lip extends radially inward from an inner wall of the rod holder.

3. The bone screw assembly of claim 2, wherein the ledge extends about an outer wall of the collet.

4. A modular bone screw comprising:
    a bone screw having a threaded shank and a screw head;
    a rod holder disposed on the screw head and configured to move relative to the screw head before the rod holder is fixed in spatial orientation relative to the bone screw, and to receive and hold a spine rod in spine rod notches disposed in a first end of the rod holder once the spatial orientation of the rod holder is fixed, the rod holder having a bore extending from the first end to a second end of the rod holder having an upper portion, inner threading on the upper portion for threaded receipt of a set screw, and a lower portion sized to receive the screw head of the bone screw, and an inner configuration on the lower portion, the inner configuration consisting of a plurality of projections each one of which extends radially inward from an inner circumference of the lower inner generally cylindrical wall; and
    a collet disposed in the interior of the rod holder, the collet having a tapered first end resting about the screw head and having a plurality of cutouts configured to allow the tapered first end of the collet to splay about the screw head and fix a spatial orientation of the rod holder relative to the bone screw through interference between the tapered first end, the screw head, and the rod holder when a spinal rod is received in and affixed to the rod holder by the set screw, the collet having a second end axially above the tapered first end and an outer configuration on an outer wall between the tapered first end and the second end that cooperates with the inner configuration of the rod holder to fix axial and rotational position of the collet relative to the rod holder, the outer configuration consisting of a plurality of depressions on a circumference of the outer wall whereby reception of the plurality of projections of the rod holder in the plurality of depressions of the collet retains the collet in its axial position;

wherein one of the rod holder and the collet includes a plurality of protuberances extending therefrom, and the other of the rod holder and collet includes a plurality of depressions that receives the plurality of protuberances to retain the collet in its position.

5. The modular bone screw of claim 4, wherein the plurality of protuberances extend radially inward from an inner wall of the rod holder.

6. The modular bone screw of claim 5, wherein the plurality of depressions are spaced apart an outer wall of the collet.

7. The modular bone screw of claim 4, wherein the plurality of protuberances comprise four radially inward projections.

8. The modular bone screw of claim 7, wherein the four radially inward projections are disposed equally about the inner circumference of the inner wall.

9. The modular bone screw of claim 8, wherein the plurality of depressions comprise four depressions.

10. The modular bone screw of claim 9, wherein the four depressions are disposed equally about the circumference of the outer wall.

* * * * *